(12) United States Patent
Chiga

(10) Patent No.: US 7,306,768 B2
(45) Date of Patent: Dec. 11, 2007

(54) FILTER FOR MEDICAL AND LABORATORY USE, ESPECIALLY FOR BLOOD ANALYSIS AND THE LIKE

(75) Inventor: Antonio Chiga, Dammartin en Goele (FR)

(73) Assignee: Filtertek Inc., Hebron, IL (US)

( * ) Notice: Subject to any disclaimer, the term of this patent is extended or adjusted under 35 U.S.C. 154(b) by 393 days.

(21) Appl. No.: 10/783,988

(22) Filed: Feb. 20, 2004

(65) Prior Publication Data
US 2004/0208796 A1 Oct. 21, 2004

(30) Foreign Application Priority Data
Feb. 21, 2003 (DE) .......................... 203 02 819 U

(51) Int. Cl.
*B01L 11/00* (2006.01)
*B01D 35/30* (2006.01)
*B65D 55/02* (2006.01)

(52) U.S. Cl. ...................... 422/101; 215/216; 215/222; 215/282; 215/289; 210/232; 210/236; 210/241

(58) Field of Classification Search ................ 210/232, 210/236, 241; 73/49.8; 215/216, 289, 222, 215/282; 422/101, 97
See application file for complete search history.

(56) References Cited

U.S. PATENT DOCUMENTS

| | | | |
|---|---|---|---|
| 1,235,438 A | 7/1917 | Chynoweth | |
| 2,381,949 A | 8/1945 | Goodloe et al. | |
| 3,085,689 A * | 4/1963 | Hering et al. | ................ 210/232 |
| 3,826,372 A | 7/1974 | Bell | |
| 3,962,524 A | 6/1976 | Miyamoto et al. | |
| 4,077,887 A | 3/1978 | Langvik | |
| 4,113,627 A * | 9/1978 | Leason | ........................ 210/446 |
| 4,159,951 A | 7/1979 | Davis | |
| 4,312,753 A | 1/1982 | Bell | |
| 4,319,996 A | 3/1982 | Vincent et al. | |
| 4,420,396 A | 12/1983 | Yamamoto et al. | |
| 4,561,977 A | 12/1985 | Sasaki | |

(Continued)

FOREIGN PATENT DOCUMENTS

DE    814 362    9/1951

(Continued)

OTHER PUBLICATIONS

SAE XX Fisita Congress, "The Automotive Future," pp. 2.154-2.161, May 1984.

(Continued)

*Primary Examiner*—Jill Warden
*Assistant Examiner*—Neil Turk
(74) *Attorney, Agent, or Firm*—Brinks Hofer Gilson & Lione

(57) ABSTRACT

A filter assembly for medical and laboratory use includes a housing. The housing includes a cover comprising an inlet and a bottom part comprising an outlet. The housing also includes a plurality of spring levers distributed around the circumference of the cover. The spring levers include hook-shaped projections, the hook-shaped projections connectable with the bottom part. The filter assembly can clamp a filter membrane or media sheet between the cover and the bottom part in a fluid-tight manner.

60 Claims, 3 Drawing Sheets

U.S. PATENT DOCUMENTS

| | | | |
|---|---|---|---|
| 4,617,121 A | | 10/1986 | Yokoyama |
| 4,618,422 A | | 10/1986 | Sasaki et al. |
| 4,743,370 A | | 5/1988 | Mizusawa |
| 4,772,044 A | | 9/1988 | Booher |
| 4,783,260 A | | 11/1988 | Kurihara |
| 4,783,321 A | * | 11/1988 | Spence ........................ 422/300 |
| 4,851,118 A | | 7/1989 | Kurihara |
| 4,874,510 A | | 10/1989 | Akira et al. |
| 4,915,831 A | * | 4/1990 | Taylor ........................ 210/232 |
| 4,961,850 A | | 10/1990 | Combest |
| 5,049,271 A | | 9/1991 | Cain |
| 5,055,187 A | | 10/1991 | Ito et al. |
| 5,084,166 A | | 1/1992 | Shiraga et al. |
| 5,169,531 A | | 12/1992 | Shiraga et al. |
| 5,174,841 A | | 12/1992 | Combest |
| 5,308,483 A | * | 5/1994 | Sklar et al. .................. 210/232 |
| 5,470,364 A | | 11/1995 | Adiletta |
| 5,474,674 A | * | 12/1995 | Bresolin et al. ........ 210/167.21 |
| 5,547,568 A | | 8/1996 | Sasaki |
| 5,556,541 A | * | 9/1996 | Ruschke ..................... 210/232 |
| 5,665,229 A | | 9/1997 | Fitzpatrick et al. |
| 5,688,460 A | * | 11/1997 | Ruschke ..................... 264/263 |
| 5,695,638 A | | 12/1997 | Gubitz et al. |
| 5,750,021 A | | 5/1998 | Liang |
| 5,795,468 A | | 8/1998 | Reising et al. |
| 5,876,599 A | | 3/1999 | Sylvester et al. |
| 5,928,507 A | | 7/1999 | Chiga |
| 6,176,133 B1 | | 1/2001 | Hutter et al. |
| 6,220,454 B1 | | 4/2001 | Chilton |
| 6,409,864 B1 | | 6/2002 | Choi |
| 6,575,309 B1 | | 6/2003 | Chiga |
| 2002/0195141 A1 | | 12/2002 | Ruschke |

FOREIGN PATENT DOCUMENTS

| | | |
|---|---|---|
| DE | 925 712 C | 8/1954 |
| DE | 26 58 358 C3 | 6/1978 |
| DE | 34 08 520 A1 | 9/1984 |
| DE | 39 14 938 C1 | 10/1990 |
| DE | 41 02 474 A1 | 8/1992 |
| DE | 295 18 501 U1 | 2/1996 |
| EP | 0 369 039 A1 | 5/1990 |
| EP | 0 396 385 A2 | 11/1990 |
| EP | 0 400 170 A | 12/1990 |
| EP | 0 475 610 B1 | 3/1992 |
| EP | 0 542 547 B1 | 5/1993 |
| EP | 0 901 571 B1 | 3/2000 |
| EP | 1 239 145 A2 | 3/2002 |
| EP | 1 239 145 A3 | 3/2002 |
| EP | 1 271 028 A2 | 1/2003 |
| EP | 1 271 028 A3 | 1/2003 |
| FR | 2 812 822 | 8/2001 |
| JP | 62-41962 | 2/1987 |
| JP | 2002-306908 A | 10/2002 |
| WO | WO 97/46800 | 12/1997 |
| WO | WO 00/03784 | 1/2000 |
| WO | WO 01/48141 A1 | 7/2001 |

OTHER PUBLICATIONS

Abstract of JP 62-41962, published Jul. 24, 1987.

"Design for assembly," http://web.archive.org/web/20021026013912/http://www.scudc.scu.edu/cmdoc/dg_doc/develop/design/part/33000004.htm (allegedly archived Oct. 26, 2002), 10 pages.

Plastics Design Library, Handbook of Plastics Joining: A Practical Guide, William Andrew, Inc., 1997, pp. 121-124.

* cited by examiner

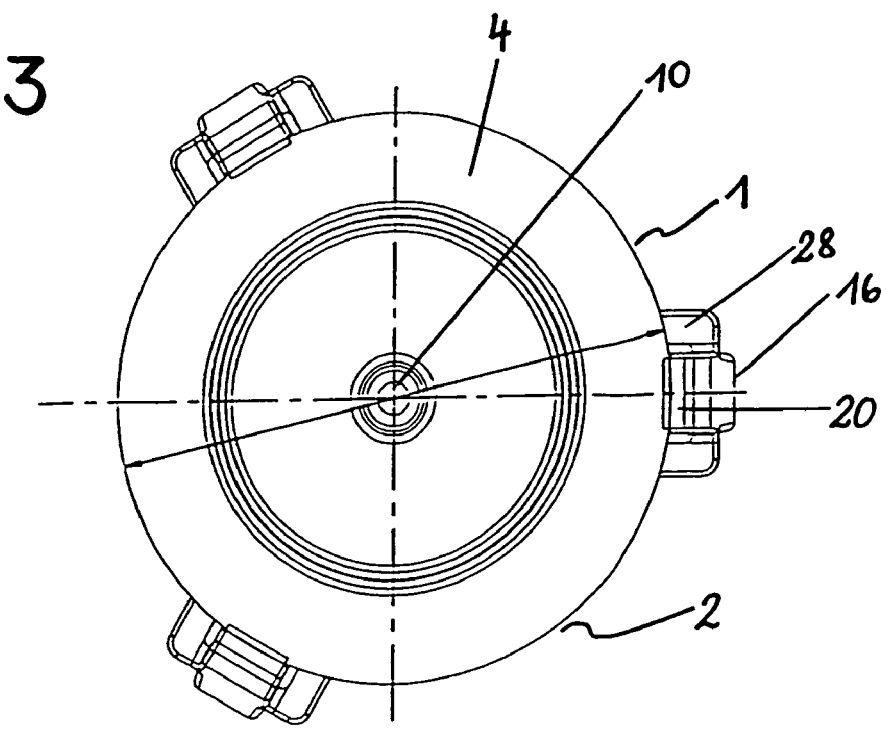
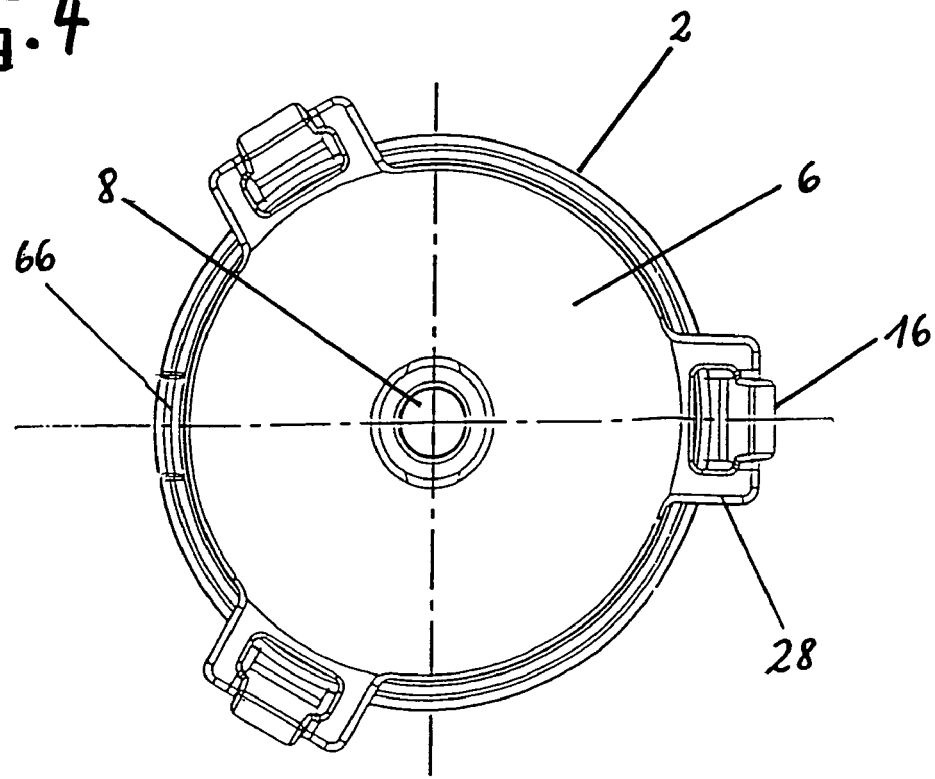

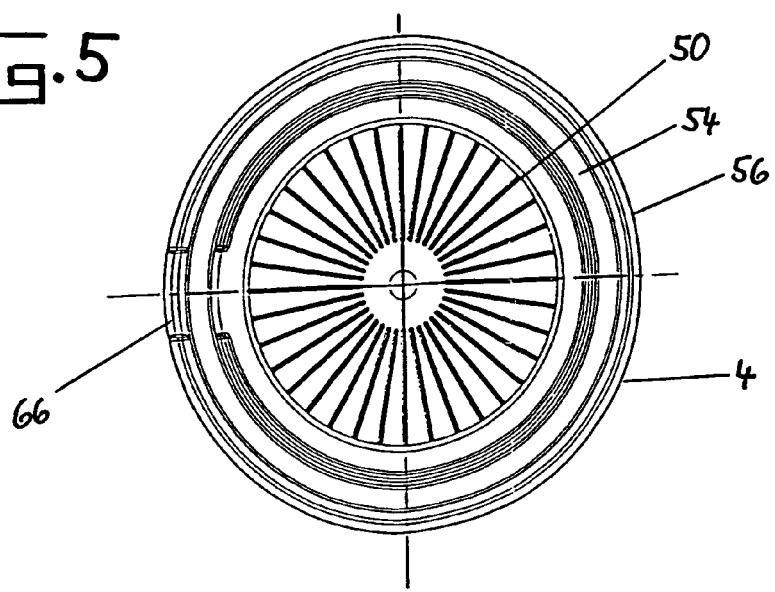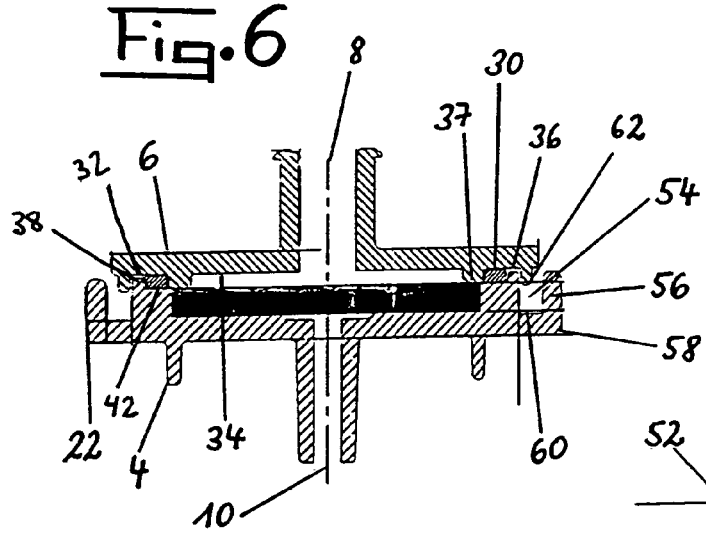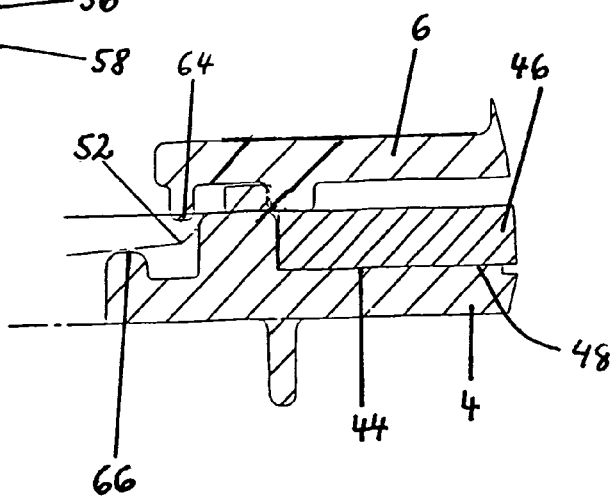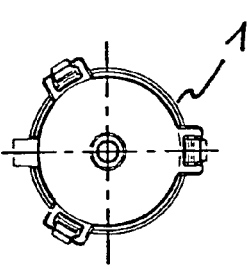

FILTER FOR MEDICAL AND LABORATORY USE, ESPECIALLY FOR BLOOD ANALYSIS AND THE LIKE

RELATED APPLICATIONS

The present patent document claims foreign priority benefits under 35 U.S.C. § 119(a)-(d) of German Application number DE 203 02 819.8, filed Feb. 21, 2003, which is hereby incorporated by reference.

FIELD OF THE INVENTION

The invention relates to a filter for medical and laboratory use, especially for blood analysis and the like.

BACKGROUND

Filters are used in the medical technical field as laboratory filters or for blood analysis, where special filter membranes are used for different tests. These filter membranes have to be exchanged quickly and frequently. Such filters are generally known and usually include a shell-shaped body as the bottom part of the housing, wherein the cover is connectable with the shell-shaped body by means of a thread forming a rotary closure. Since such filters have housings with a diameter of about 30 mm, the thread connection between the cover and the housing bottom part is extremely cumbersome, and additionally there is the danger that, when closing the rotary cover, the filter membrane can be deformed. The manufacture of the housings for such filters is comparatively difficult since rotary cores have to be used in the injection molding tools to enable to demold one of the two thread parts, i.e. the interior thread. The costs of the tools to be produced for this purpose are comparatively high.

Thus, it is desired to improve a filter of the above identified kind in such a way that the drawbacks of the prior art are avoided and that the production thereof is much more economical.

BRIEF SUMMARY

In one aspect, a filter assembly for medical and laboratory use includes a housing. The housing includes a cover with an inlet and a bottom part with an outlet. The housing also includes a plurality of spring levers distributed around the circumference of the cover. The spring levers include hook-shaped projections, the hook-shaped projections connectable with the bottom part. The filter assembly can clamp a filter membrane between the cover and the bottom part in a fluid-tight manner.

In another aspect, the bottom part includes a bottom rim. The hook-shaped projections overlap the bottom rim of the bottom part to releasably attach thereto. The spring levers rotate on pivot points, and the spring levers include upwardly projecting actuation flaps.

In another aspect, the spring levers and the cover are formed unitarily of plastic. The spring levers are molded onto flaps laterally projecting from the cover. The flaps form the pivot points of the spring levers.

In another aspect, the filter assembly includes an annular seal between the cover and the bottom part. The cover includes an annular channel and a free annular space. The bottom part comprises an annular projection engaging the free annular space. The annular seal is disposed in the annular channel.

In another aspect, the filter membrane includes a lateral tongue extending from the closed housing. The cover and the bottom part each includes a recess for the passage of the tongue of the filter membrane.

The filter assembly of the present invention can be assembled by simply pressing the housing components together such that the filter membrane is neither deformed nor damaged. Additionally, the two housing parts can be produced far less costly by injection molding. The filter housing can be opened easily to enable an exchange of the filter membrane. The filter membrane, during replacement, can be easily inserted and fixed. The tongue projecting from the housing can be used for the identification of the filter membrane in the filter housing.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

FIG. 3 is a bottom view of the filter assembly.

FIG. 4 is a top view of the filter assembly.

FIG. 5 is a top view OF the bottom part of the filter assembly.

FIG. 6 is a cross-sectional view along the line A-A in FIG. 2.

FIG. 7 is a cross-sectional view of part of the filter assembly.

FIG. 8 is a side view and top view of the filter assembly.

DETAILED DESCRIPTION OF THE DRAWINGS AND THE PRESENTLY PREFERRED EMBODIMENTS

Figure 1:
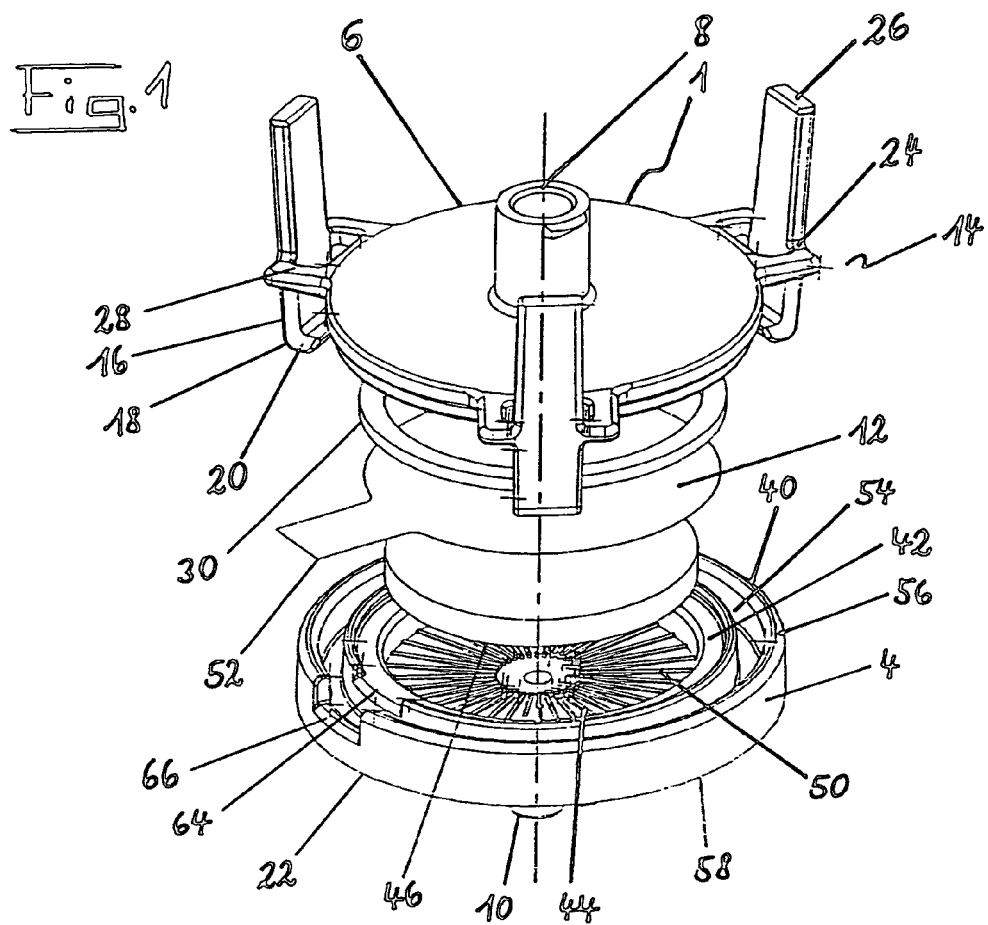
FIG. 1 is an exploded perspective view of a filter assembly.
Figure 2:
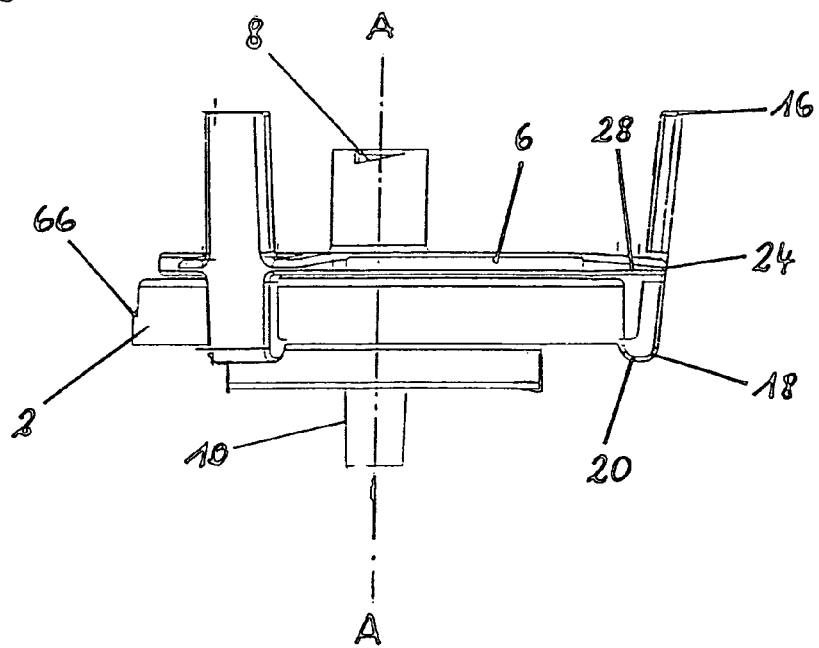
FIG. 2 is a side view of the closed filter assembly.

It should be understood that in certain instances details have been omitted which are not necessary for an understanding of the present invention, such as conventional details of fabrication and assembly.

As shown in FIGS. 1 to 4, the filter 1 according to the invention has a two-part housing 2 which includes a bottom part 4 and a cover 6. The housing 2 is preferably made of plastic. The cover 6 has a central inlet 8 which, in one embodiment, is a female Luer-Lock-connection. The bottom part 4 has an outlet 10 which, in one embodiment, is a male Luer-Lock-connection. An exchangeable filter membrane 12 is clamped between the cover 6 and the bottom part 4. A connector 14 is provided to connect the cover 6 with the bottom part 4 in a fluid-tight manner.

According to one aspect of the invention, the connector 14 includes a number of spring levers 16 distributed around the circumference of the cover. The free bottom ends 18 of the spring levers 16 include inwardly projecting hook-shaped projections 20 which are connectable with the bottom part 4. The hook-shaped projections 20 overlap the bottom rim 22 of the bottom part 4 when the housing 2 is in a closed position. This creates a pressure force between the cover 6 and the bottom part 4, by shown in FIGS. 2 to 4. The arrangement is such that the spring levers 16 are resiliently pretensioned in the closing direction.

To enable the opening of the housing 2 of the filter 1 to exchange the filter membrane 12, the spring levers 16 include upwardly projecting actuation flaps 26 above their pivot point 24. By pressing the actuation flaps 26 together against the inwardly directed pretension of the spring levers 16, the cover 6 can be easily removed from the bottom part 4. Thus, the filter housing 2 can be easily opened to exchange the filter membrane.

In one embodiment, the spring levers 16 are of unitary construction with the cover 6. The spring levers 16 are molded onto bow-shaped flaps 28 which laterally project from the cover 6. The spring levers 16 and bow-shaped flaps 28 are preferably molded from plastic. The elastic properties of the plastic used create a spring force and the construction of the device is drastically simplified. The flaps 28 form the pivot point 24 of the spring levers 16 and simultaneously produce the spring pretension of the spring levers 16 directed inwardly to the central axis of the housing 2. In a preferred embodiment, three spring levers 16 are distributed around the circumference of the cover 6 at equal distances. This kind of three-point fastening assures contact of the cover 6 at the bottom part 4.

It will be apparent to those skilled in the art that the arrangement could be inverted by molding the spring levers 16 onto the bottom part 4. The spring levers 16 then would overlap the upper rim of the cover 6. For practical reasons, i.e. for facilitating the use and the separation of the cover 6 from the bottom part, the arrangement shown, however, is preferred, in which the spring levers 16 are provided on the cover 6.

As can be seen in FIGS. 1 and 6 a compressible annular seal 30 is disposed between the cover 6 and the bottom part 4. The compressible annular seal 30 is positioned or fixed in an annular channel 32 in the bottom side 34 of the cover 6. The channel 32 is limited on its side radially outward from the annular seal 30 by an annular projection 62 which defines a free annular space 36 between the annular seal 30 and the projection 62. On the radially inward side, the channel 32 is limited by an annular bulge 37 contacting the annular seal 30 which, as can be seen in FIG. 6, is in contact with the filter membrane 12. An annular projection 38 on the top side 40 of the bottom part 4 engages into the free annular space 36. The annular projection 38 simultaneously surrounds a contact surface 32 as a counter-face for the annular seal 30. When assembling the filter housing, the annular projection 62 and the annular bulge 37 automatically center the cover with respect to the bottom part.

As can be seen in FIGS. 1 and 6, the diameter of the filter membrane 12 is adapted to the interior diameter of the annular projection 38 such that with the housing 2 closed, the circumference of the filter membrane 12 is clamped between the annular seal 30 and the contact surface 42. A suitable and straight fixing of the filter membrane 12 is thereby achieved.

As can be further seen in FIGS. 1, 5 and 6, the bottom part 4 has a recess 44 within the contact area 42. A disk-shaped supporting body 46 for the filter membrane 12 is disposed in the recess 44. The disk-shaped supporting body 46 is preferably of a porous material. With the housing 2 closed, therefore, the filter membrane 12 is clamped at its rim between the annular seal 30 and the contact surface 42. At the same time, the central area of the filter membrane 12 is supported by the supporting body 46. The supporting body 46 prevents the filter membrane from bending during filtration.

As can be seen in FIGS. 1 and 5, the bottom 48 of the recess 44 in the bottom part 4 is preferably provided with supporting ribs 50 for the supporting body 46. The supporting ribs 50 surround the central outlet 10 in a star-shaped arrangement.

In a preferred embodiment shown in FIGS. 1 and 7, the filter membrane 12 includes a tongue 52 which projects laterally from the closed housing. The tongue 52 provides for improved handling of the filter membrane 12 during the exchange thereof. The tongue 52 also allows easy visual identification of the filter membrane within the housing during exchange or during analysis or work.

From FIGS. 1, 5 and 6, it can be seen that radially outward of the annular projection 38 at the bottom part 4 there is provided a further annular channel 54, the exterior wall 56 of which is engaged by the hook-shaped projections 20 of the spring levers 16 at its outer bottom edge 58. The bottom 60 of the annular channel 54 is positioned at about the height of the bottom 48 of the recess 44. This arrangement has the advantage that the part of the housing carrying the filter membrane is not influenced by the clamping forces exerted by the spring levers. Additionally, the annular channel 54 can capture remaining filtrate or fluid during the exchange of the filter membrane.

As shown in the cross-sectional view according to FIGS. 6 and 7, the annular channel 54 receives the projection 62, limiting the free annular space 36 at the cover 6 on the outer side. As can be seen from the enlarged detail view according to FIG. 7 and from the top view of the bottom part 4, FIG. 5, the projection 62 limits the free annular space 36. The cover 6 and bottom part 4 each has a recess 64 and 66, respectively, which receive the tongue 52 of the filter membrane 12 outwardly projecting from the housing 2. The recesses 64 and 66 prevent deformation of the filter membrane in the area of the tongue.

A preferred embodiment may include the following materials. Bottom part 4 and cover 6 are preferably monolithic molded plastic resin, preferably of plastic type M.A.B.S. (methyl methacrylate acrylonitrile butadiene styrene resin). It is to be noted that this plastic material is illustrative and many other suitable materials well known in the art could be used, including PP (polypropylene resins), POM (acetal copolymer resins), PC (polycarbonate resins), and PA (polyamide resins) suitable for the fluid sterilization protocol, if any, and operating temperature envisioned for the operating environment of the particular assembly application. It is to be further noted that the plastic resin may be opaque or transparent. Annular seal 30 is preferably of nitrile rubber 70 shore hardness, however it can be made from other types of material or rubber and varying hardness depending upon the application and liquid filtered, such as liquid silicone, silicone rubber or natural rubber, and may be O-ring, flat, or a variety of shapes and cross-sections well known in the art. Supporting body 46 is preferably a porous disk of high density polyethylene, and other inert plastics may be used so long as there is no damage to the filter membrane and flow characteristics are not unduly compromised. Alternatively, the porous disk can be replaced by radial and/or annular ribs with suitable channels communicating with the outlet on, or molded onto, bottom plastic part 4. Filter membrane 12 is preferably PC (polycarbonate), PTFE (polytetrafluoroethylene), or polyester of porosity 0.45 micron, and the porosity may vary from 0.2 to 10 micron. In addition, filter membrane 12 may be substituted with other media such as woven screen, again as suitable for the intended application.

The embodiments described above and shown herein are illustrative and not restrictive. In certain cases, materials of construction have not been described; in these cases, it is to be understood that the invention may be made by any known method and of any known material. The scope of the invention is indicated by the claims rather than by the foregoing description and attached drawings. The invention may be embodied in other specific forms without departing from the spirit of the invention. Accordingly, these and any other changes which come within the scope of the claims are intended to be embraced therein.

The invention claimed is:

1. A filter assembly for medical and laboratory use comprising a housing, the housing comprising:
a plastic cover having a perimeter and comprising an inlet;
a bottom part having an underside and comprising an outlet; and
a plurality of plastic spring levers distributed around the perimeter of the cover and unitarily formed with the plastic cover, the spring levers rotatable at pivot points and including hook-shaped projections projecting inwardly relative to the cover perimeter on one side of the pivot points and actuation flaps on the other side of the pivot points, wherein the spring levers are resiliently pre-tensioned to direct the hook-shaped projections inwardly relative to the cover perimeter and the hook-shaped projections releasably overlapping and attaching to the bottom part underside upon actuation of the actuation flaps, wherein the filter assembly is adapted to clamp a filter membrane between the cover and the bottom part in a fluid-tight manner when the hook-shaped projections overlap and attach to the bottom part underside.

2. A filter assembly according to claim 1, wherein the perimeter of the cover has a circumference and the underside of the bottom part comprises a bottom rim, and wherein the hook-shaped projections overlap the underside of the bottom rim of the bottom part to releasably attach thereto, and wherein the spring levers are adapted to rotate about the pivot points upon actuation of the upwardly projecting actuation flaps in a radial direction relative to the circumference of the cover.

3. A filter assembly according to claim 2, wherein the spring levers are molded onto flaps laterally projecting from the cover, which flaps form the pivot points of the spring levers.

4. A filter assembly according to claim 3, wherein the plurality of spring levers comprises three spring levers distributed equidistantly around the circumference of the cover.

5. A filter assembly according to claim 4, further comprising an annular seal between the cover and the bottom part, wherein the cover has an annular channel and a free annular space, and wherein the bottom part comprises an annular projection engaging the free annular space, wherein the annular seal is disposed in the annular channel.

6. A filter assembly according to claim 5, wherein a disk-shaped supporting body for the filter membrane is disposed in a recess of the bottom part, and wherein the recess comprises supporting ribs surrounding the outlet.

7. A filter assembly according to claim 6, wherein the supporting body comprises a porous material.

8. A filter assembly according to claim 7, wherein the filter membrane comprises a lateral tongue extending from the closed housing.

9. A filter assembly according to claim 8, wherein the bottom part has an annular channel defined in part by an exterior wall and a bottom, which exterior wall is overlapped by the hook-shaped projections and wherein the bottom of the annular channel is positioned generally at a same height as a height of the bottom of the recess.

10. A filter assembly according to claim 9, wherein the cover and the bottom part each further comprises a recess for the passage of the tongue of the filter membrane.

11. A filter assembly according to claim 5, wherein the filter membrane comprises a lateral tongue extending from the closed housing.

12. A filter assembly according to claim 11, wherein the bottom part has an annular channel defined in part by an exterior wall and a bottom, which exterior wall is overlapped by the hook-shaped projections.

13. A filter assembly according to claim 12, wherein the cover and the bottom part each further comprises a recess for the passage of the tongue of the filter membrane.

14. A filter assembly according to claim 5, wherein the bottom part an annular channel defined in part by an exterior wall and a bottom, which exterior wall is overlapped by the hook-shaped projections.

15. A filter assembly according to claim 14, wherein the cover and the bottom part each further comprises a recess for the passage of a tongue of the filter membrane.

16. A filter assembly according to claim 1, wherein the cover has a circumference and the plurality of spring levers comprises three spring levers distributed equidistantly around the circumference of the cover.

17. A filter assembly according to claim 16, further comprising an annular seal between the cover and the bottom part, wherein the cover has an annular channel and a free annular space, and wherein the bottom part comprises an annular projection engaging the free annular space, wherein the annular seal is disposed in the annular channel.

18. A filter assembly according to claim 17, further comprising an annular projection such that with the housing closed a circumferential rim of the filter membrane is clamped between the annular seal and a contact surface of the bottom part, and further comprising a disk-shaped supporting body for the filter membrane, and the bottom part further comprising a recess wherein the disk-shaped supporting body for the filter membrane is disposed in the recess of the bottom part, and wherein the recess further comprises supporting ribs surrounding the outlet.

19. A filter assembly according to claim 18, wherein the supporting body comprises a porous material.

20. A filter assembly according to claim 19, wherein the filter membrane comprises a lateral tongue extending from the closed housing.

21. A filter assembly according to claim 20, wherein the bottom part has an annular channel defined in part by an exterior wall and a bottom, which exterior wall is overlapped by the hook-shaped projections and wherein the bottom of the annular channel is positioned generally at a same height as a height of the bottom of the recess.

22. A filter assembly according to claim 21, wherein the cover and the bottom part each further comprises a recess for the passage of the tongue of the filter membrane.

23. A filter assembly according to claim 17, wherein the filter membrane comprises a lateral tongue extending from the closed housing.

24. A filter assembly according to claim 23, wherein the bottom part has an annular channel defined in part by an exterior wall and a bottom, which exterior wall is overlapped by the hook-shaped projections.

25. A filter assembly according to claim 24, wherein the cover and the bottom part each further comprises a recess for the passage of the tongue of the filter membrane.

26. A filter assembly according to claim 17, wherein the bottom part has an annular channel defined in part by an exterior wall and a bottom, which exterior wall is overlapped by the hook-shaped projections.

27. A filter assembly according to claim 26, wherein the cover and the bottom part each further comprises a recess for the passage of a tongue of the filter membrane.

28. A filter assembly according to claim 1, wherein the spring levers are molded onto members laterally projecting from the cover, which flaps form the pivot points of the spring levers.

29. A filter assembly according to claim 28, wherein the cover has a circumference and the plurality of spring levers comprises three spring levers distributed equidistantly around the circumference of the cover.

30. A filter assembly according to claim 29, further comprising an annular seal between the cover and the bottom part, wherein the cover has an annular channel and a free annular space, and wherein the bottom part comprises an annular projection engaging the free annular space, wherein the annular seal is disposed in the annular channel.

31. A filter assembly according to claim 30, further comprising an annular projection such that with the housing closed a circumferential rim of the filter membrane is clamped between the annular seal and a contact surface of the bottom part, wherein the bottom part further includes a recess, and wherein the recess comprises supporting ribs surrounding the outlet.

32. A filter assembly according to claim 31, wherein the supporting body comprises a porous material.

33. A filter assembly according to claim 32, wherein the filter membrane comprises a lateral tongue extending from the closed housing.

34. A filter assembly according to claim 33, wherein the bottom part has an annular channel defined in part by an exterior wall and a bottom, which exterior wall is overlapped by the hook-shaped projections and wherein the bottom of the annular channel is positioned generally at a same height as a height of the bottom of the recess.

35. A filter assembly according to claim 34, wherein the cover and the bottom part each further comprises a recess for the passage of the tongue of the filter membrane.

36. A filter assembly according to claim 1, further comprising an annular seal between the cover and the bottom part, wherein the cover has an annular channel and a free annular space, and wherein the bottom part comprises an annular projection engaging the free annular space, wherein the annular seal is disposed in the annular channel.

37. A filter assembly according to claim 36, wherein the filter membrane comprises a lateral tongue extending from the closed housing.

38. A filter assembly according to claim 37, wherein the bottom part has an annular channel defined in part by an exterior wall and a bottom, which exterior wall is overlapped by the hook-shaped projections.

39. A filter assembly according to claim 38, wherein the cover and the bottom part each further comprises a recess for the passage of a tongue of the filter membrane.

40. A filter assembly according to claim 36, further comprising an annular projection such that with the housing closed a circumferential rim of the filter membrane is clamped between the annular seal and a contact surface of the bottom part, wherein the bottom part further includes a recess, and wherein the recess comprises supporting ribs surrounding the outlet.

41. A filter assembly according to claim 40, wherein the supporting body comprises a porous material.

42. A filter assembly according to claim 41, wherein the filter membrane comprises a lateral tongue extending from the closed housing.

43. A filter assembly according to claim 42, wherein the bottom part has an annular channel defined in part by an exterior wall and a bottom, which exterior wall is overlapped by the hook-shaped projections and wherein the bottom of the annular channel is positioned generally at a same height as a height of the bottom of the recess.

44. A filter assembly according to claim 43, wherein the cover and the bottom part each further comprises a recess for the passage of the tongue of the filter membrane.

45. A filter assembly according to claim 1, wherein the filter membrane comprises a lateral tongue extending from the closed housing.

46. A filter assembly according to claim 45, wherein the bottom part has an annular channel defined in part by an exterior wall and a bottom, which exterior wall is overlapped by the hook-shaped projections.

47. A filter assembly according to claim 46, wherein the cover and the bottom part each comprises a recess for the passage of the tongue of the filter membrane.

48. A filter assembly according to claim 1, wherein the bottom part has an annular channel defined in part by an exterior wall and a bottom, which exterior wall is overlapped by the hook-shaped projections.

49. A filter assembly according to claim 48, wherein the cover and the bottom part each further comprises a recess for the passage of a tongue of the filter membrane.

50. A filter assembly for medical and laboratory use and adapted to receive a filter media sheet, the filter assembly comprising:
 a plastic cover having a perimeter and comprising an inlet;
 a bottom part having an underside and comprising an outlet;
 a means for supporting the filter media sheet; and
 a plurality of plastic spring levers distributed around the perimeter of the cover and unitarily formed with the plastic cover, the spring levers rotatable at pivot points and including hook-shaped projections oriented inwardly relative to the perimeter and on one side of the pivot points and actuation flaps on the other side of the pivot points, wherein the spring levers are resiliently pre-tensioned to direct the hook-shaped projections inwardly relative to the cover perimeter and the hook-shaped projections releasably overlapping and attaching to the bottom part underside upon actuation of the flaps, wherein the filter assembly is adapted to clamp a filter media sheet between the cover and the bottom part in a fluid-tight manner when the hook-shaped projections overlap and attach to the bottom part underside.

51. A filter assembly according to claim 50, wherein the perimeter of the cover has a circumference and the underside of the bottom part comprises a bottom rim, and wherein the hook-shaped projections overlap the underside of the bottom rim of the bottom part to releasably attach thereto, and wherein the spring levers are adapted to rotate about the pivot points upon actuation of the upwardly projecting actuation flaps in a radial direction relative to the circumference of the cover.

52. A filter assembly according to claim 50, further comprising an annular seal between the cover and the bottom part, wherein the cover has an annular channel and a free annular space, and wherein the bottom part comprises an annular projection engaging the free annular space, wherein the annular seal is disposed in the annular channel.

53. A filter assembly according to claim 50, wherein the means for supporting the filter media comprises a disk-shaped supporting body for the filter media sheet disposed in a recess of the bottom part, and wherein the recess comprises supporting ribs surrounding the outlet.

54. A filter assembly according to claim 50 wherein the means for supporting the filter media comprises a plurality of ribs.

55. A filter assembly according to claim 50, wherein the filter media sheet comprises a lateral tongue extending from the closed housing.

56. A filter assembly according to claim 55, wherein the cover and the bottom part each further comprises a recess for the passage of the tongue of the filter media sheet.

57. A filter assembly according to claim 51, wherein the means for supporting the filter media comprises a disk-shaped supporting body for the filter media sheet disposed in a recess of the bottom part, and wherein the recess comprises supporting ribs surrounding the outlet.

58. A filter assembly according to claim 51 wherein the means for supporting the filter media comprises a plurality of ribs.

59. A filter assembly according to claim 52, wherein the means for supporting the filter media comprises a disk-shaped supporting body for the filter media sheet disposed in a recess of the bottom part, and wherein the recess comprises supporting ribs surrounding the outlet.

60. A filter assembly according to claim 52 wherein the means for supporting the filter media comprises a plurality of ribs.

* * * * *